(12) United States Patent
Heil, Jr. et al.

(10) Patent No.: US 7,110,815 B2
(45) Date of Patent: Sep. 19, 2006

(54) SYSTEM AND METHOD FOR PROVIDING TEMPORARY STIMULATION THERAPY TO OPTIMIZE CHRONIC ELECTRICAL PERFORMANCE FOR ELECTRODES USED IN CONJUNCTION WITH A CARDIAC RHYTHM MANAGEMENT SYSTEM

(75) Inventors: Ronald W. Heil, Jr., Roseville, MN (US); Bruce H. Kenknight, Maple Grove, MN (US)

(73) Assignee: Cardiac Pacemakers, Inc., Saint Paul, MN (US)

( * ) Notice: Subject to any disclaimer, the term of this patent is extended or adjusted under 35 U.S.C. 154(b) by 622 days.

(21) Appl. No.: 10/139,916

(22) Filed: May 6, 2002

(65) Prior Publication Data

US 2003/0208236 A1 Nov. 6, 2003

(51) Int. Cl.
 *A61N 1/362* (2006.01)
(52) U.S. Cl. .......................................... 607/11; 607/28
(58) Field of Classification Search ................ 607/1–5, 607/8–9, 11, 27–28; 604/20
 See application file for complete search history.

(56) References Cited

U.S. PATENT DOCUMENTS

| | | | |
|---|---|---|---|
| 3,915,174 A * | 10/1975 | Preston | 607/9 |
| 4,117,848 A | 10/1978 | Naylor | |
| 4,248,238 A | 2/1981 | Joseph | |
| 4,497,326 A | 2/1985 | Curry | |
| 4,558,702 A | 12/1985 | Barreras et al. | |
| 4,603,705 A | 8/1986 | Speicher et al. | |
| 4,628,934 A | 12/1986 | Pohndorf et al. | |
| 4,641,656 A | 2/1987 | Smits | |
| 4,708,145 A | 11/1987 | Tacker, Jr. et al. | |
| 4,741,342 A * | 5/1988 | Stotts | 607/30 |
| 4,745,923 A * | 5/1988 | Winstrom | 607/9 |
| 4,819,661 A | 4/1989 | Heil, Jr. et al. | |
| 4,821,723 A | 4/1989 | Baker, Jr. et al. | |
| 4,858,610 A | 8/1989 | Callaghan et al. | |
| 4,858,623 A | 8/1989 | Bradshaw et al. | |

(Continued)

FOREIGN PATENT DOCUMENTS

DE 19930264 12/2000

OTHER PUBLICATIONS

Burr, H. S., S. C. Harvey, and M. Taffel, Bio-electric Correlates of wound Healing, 11 Yale J. Biol. Med., 1938, pp. 103-107.

(Continued)

*Primary Examiner*—Robert E. Pezzuto
*Assistant Examiner*—Kristen Mullen
(74) *Attorney, Agent, or Firm*—Schwegman, Lundberg, Woessner & Kluth, P.A.

(57) ABSTRACT

A system and method for stimulating a human heart including a sensing module coupled through a lead to an electrode associated with a tissue of the human heart for sensing electrical activity of the heart. A controller module may be coupled to the sensing module. The controller module may select between a temporary stimulation therapy and a chronic stimulation therapy. Also included is a therapy module coupled to the controller, the therapy module communicating a plurality of anodic pulses to the heart through the lead when providing the temporary stimulation therapy. The amplitude, frequency, and duration of the anodic pulses may be varied, and biphasic pacing may also be used. The electrode may be a drug-eluting electrode for delivery of a drug. After an event occurs, the controller module may transition to the chronic stimulation therapy that may include cathodic stimulation.

33 Claims, 9 Drawing Sheets

U.S. PATENT DOCUMENTS

| | | | |
|---|---|---|---|
| 4,913,164 | A | 4/1990 | Greene et al. |
| 4,928,688 | A | 5/1990 | Mower |
| 5,050,601 | A | 9/1991 | Kupersmith et al. |
| 5,087,243 | A * | 2/1992 | Avitall .................. 604/20 |
| 5,190,052 | A | 3/1993 | Schroeppel |
| 5,243,978 | A | 9/1993 | Duffin, Jr. |
| 5,265,602 | A | 11/1993 | Anderson et al. |
| 5,269,319 | A | 12/1993 | Schulte et al. |
| 5,281,219 | A | 1/1994 | Kallok |
| 5,311,966 | A | 5/1994 | Daniels |
| 5,314,430 | A | 5/1994 | Bardy |
| 5,324,309 | A | 6/1994 | Kallok |
| 5,328,442 | A | 7/1994 | Levine |
| 5,330,506 | A | 7/1994 | Alferness et al. |
| 5,331,966 | A | 7/1994 | Bennett et al. |
| 5,336,253 | A | 8/1994 | Gordon et al. |
| 5,344,429 | A | 9/1994 | Smits |
| 5,370,665 | A | 12/1994 | Hudrlik |
| 5,385,574 | A | 1/1995 | Hauser et al. |
| 5,391,200 | A | 2/1995 | KenKnight et al. |
| 5,403,356 | A | 4/1995 | Hill et al. |
| 5,405,375 | A | 4/1995 | Ayers et al. |
| 5,411,528 | A | 5/1995 | Miller et al. |
| 5,423,873 | A | 6/1995 | Neubauer et al. |
| 5,431,681 | A | 7/1995 | Helland |
| 5,466,254 | A | 11/1995 | Helland |
| 5,470,342 | A * | 11/1995 | Mann et al. .................. 607/5 |
| 5,487,758 | A | 1/1996 | Hoegnelid et al. |
| 5,501,702 | A | 3/1996 | Plicchi et al. |
| 5,501,703 | A | 3/1996 | Holsheimer et al. |
| 5,507,781 | A | 4/1996 | Kroll et al. |
| 5,531,764 | A | 7/1996 | Adams et al. |
| 5,571,163 | A | 11/1996 | Helland |
| 5,584,865 | A | 12/1996 | Hirschberg et al. |
| 5,634,899 | A * | 6/1997 | Shapland et al. .......... 604/507 |
| 5,649,966 | A | 7/1997 | Noren et al. |
| 5,720,768 | A | 2/1998 | Verboven-Nelissen |
| 5,766,230 | A | 6/1998 | Routh et al. |
| 5,792,203 | A | 8/1998 | Schroeppel |
| 5,792,208 | A | 8/1998 | Gray |
| 5,797,967 | A | 8/1998 | KenKnight |
| 5,800,464 | A * | 9/1998 | Kieval .......................... 607/9 |
| 5,800,465 | A | 9/1998 | Thompson et al. |
| 5,814,079 | A * | 9/1998 | Kieval .......................... 607/4 |
| 5,836,981 | A | 11/1998 | Chang et al. |
| 5,843,132 | A | 12/1998 | Ilvento |
| 5,861,013 | A | 1/1999 | Peck et al. |
| 5,895,416 | A | 4/1999 | Barreras, Sr. et al. |
| 5,928,269 | A | 7/1999 | Alt |
| 5,935,160 | A | 8/1999 | Auricchio et al. |
| 5,978,705 | A | 11/1999 | KenKnight et al. |
| 5,995,870 | A | 11/1999 | Cazeau et al. |
| 5,999,849 | A | 12/1999 | Gord et al. |
| 5,999,853 | A | 12/1999 | Stoop et al. |
| 6,002,962 | A | 12/1999 | Huang et al. |
| 6,047,211 | A | 4/2000 | Swanson et al. |
| 6,067,470 | A | 5/2000 | Mower |
| 6,070,100 | A | 5/2000 | Bakels et al. |
| 6,081,748 | A | 6/2000 | Struble et al. |
| 6,085,118 | A | 7/2000 | Hirschberg et al. |
| 6,094,596 | A | 7/2000 | Morgan |
| 6,104,953 | A | 8/2000 | Leyde |
| 6,115,630 | A | 9/2000 | Stadler et al. |
| 6,178,351 | B1 | 1/2001 | Mower |
| 6,185,459 | B1 | 2/2001 | Mehra et al. |
| 6,219,579 | B1 | 4/2001 | Bakels et al. |
| 6,219,582 | B1 | 4/2001 | Hofstad et al. |
| 6,223,079 | B1 | 4/2001 | Bakels et al. |
| 6,223,082 | B1 | 4/2001 | Bakels et al. |
| 6,233,487 | B1 | 5/2001 | Mika et al. |
| 6,238,420 | B1 | 5/2001 | Bakels et al. |
| 6,275,730 | B1 | 8/2001 | KenKnight et al. |
| 6,282,444 | B1 * | 8/2001 | Kroll et al. .................... 607/3 |
| 6,292,693 | B1 | 9/2001 | Darvish et al. |
| 6,295,470 | B1 | 9/2001 | Mower |
| 6,317,632 | B1 | 11/2001 | Krig et al. |
| 6,337,995 | B1 * | 1/2002 | Mower .......................... 607/5 |
| 6,341,234 | B1 | 1/2002 | Thong et al. |
| 6,343,232 | B1 | 1/2002 | Mower |
| 6,366,808 | B1 | 4/2002 | Schroeppel et al. |
| 6,370,427 | B1 | 4/2002 | Alt et al. |
| 6,400,992 | B1 | 6/2002 | Borgersen et al. |
| 6,456,878 | B1 | 9/2002 | Yerich et al. |
| 6,493,582 | B1 | 12/2002 | Ripart et al. |
| 6,539,260 | B1 | 3/2003 | Schloss |
| 6,556,873 | B1 | 4/2003 | Smits |
| 6,574,512 | B1 | 6/2003 | Zhang et al. |
| 6,584,362 | B1 | 6/2003 | Scheiner et al. |
| 6,587,721 | B1 * | 7/2003 | Prutchi et al. .................. 607/9 |
| 6,640,135 | B1 | 10/2003 | Salo et al. |
| 6,738,669 | B1 | 5/2004 | Sloman et al. |
| 6,788,971 | B1 | 9/2004 | Sloman et al. |
| 2002/0068959 | A1 | 6/2002 | Warren et al. |
| 2002/0151938 | A1 | 10/2002 | Corbucci |

OTHER PUBLICATIONS

DeCaprio, V., P. Hurzeler, and S. Furman, A Comparison of Unipolar and Bipolar Electrograms for Cardiac Pacemaker Sensing, Circ., 56, 1977, p. 750-5.

Varriale, P., and R. P. Kwa, The Ventricular Electrogram, Chap. 5 in *Modem Cardiac Pacing*, S.S. Barold, ed., Futura Publ. Co., Mount Kisco, NY, 1985.

Kay, G. N., *Cardiac Pacing, Practical Cardiac Diagnosis*, pp. 62-65, 2nd ed., Ellenbogen, K. A., ed., Blackwell Science, Cambridge, MA, 1996.

Bassett, C. A. L., R. J. Pawluk, and R. O. Becker, Effects of Electric Currents on Bone, *In Vivo*, Nature, 204, 1964, p. 65204.

Bassett, C. A., and R. J. Pawluk, Noninvasive Methods for Stimulating Osteogenesis, J. Biomed. Mater. Res., 9, 1975, p. 3714.

Chakkalakal, D. A., L. Lippiello, R. L. Shindell, and J. F. Connolly, Electrophysiology of DirectCurrent Stimulation of Fracture Healing in Canine Radium, IEEE Trans. Biomed. Eng., 37, 1990, p. 1048-58.

Assimacopoulos, A., Wound Healing Promotion by the Use of Negative Electric Current, Amer. Surg., 34, 1968, p. 423-31.

Konikoff, J. J., Electrical Promotion of soft Tissue Repair, Ann. Biomed. Eng., 4, 1976, p. 1-5.

Alvarez, O. M., P. M. Mertz, R. V. Smerbeck, and W. H. Eaglstein, The Healing of Superficial Skin Wounds Is Stimulated by External Electrical Current, J. Invest. Dermatol., 81, 1983, p. 144-8.

Carley, P. J., and S. F. Wainapel, Electrotherapy for Acceleration of Wound Healing: Low Intensity Direct Current, Arch. Phys. Med. Rehabil., 66, 1985, p. 443-6.

Kloth, L. C., and J. A. Feedar, Acceleration of Wound Healing with High Voltage, Monophasic, Pulsed Current, Physical Therapy, 68, 1988, p. 503-8.

Weiss, D. S., W. H. Eaglstein, and V. Falanga, Exogenous Electric Current Can Reduce the Formation of Hypertrophic Sears, J. Dermatol Surg. Oncol, 15, 1989, p. 1272-5.

Dunn, M, C. J. Doillon, R. A. Berg, R. M. Olson, F. H. Silver, Wound Healing Using a Collagen Matrix: Effects of DC Electrical Stimulation, J. Biomed. Mater. Res., 22, 1988, p. 191-206.

Salman, N. N., and J. B. Park, The Effect of Direct Electrical Current Stimulation on the Bone/Porous Metallic Implant Interface, Biomaterials, 1, 1980, p. 209-13.

Ågren, M. S., M. A. Engel, and P. M. Mertz, Collagenase During Burn Wound Healing: Influence of a Hydrogel Dressing and Pulsed Electrical Stimulation, Plast. Reconstr. Surg., 94, 1994, p. 518-24.

Jiang, H., [Acceleration of Epidermis Proliferation by Direct Current Stimulation], Chung Hua Cheng Hsing Shao Shang, 8, 1992, 136-8. Abstract only.

Roy, O. Z., H. A. Heggtveit, and W. G. Waddell, Electrical and Pathological Observations on the Response of the Canine Heart to Cardiac Pacing, Br. J. Surg., 55, 1968, p. 861-2.

Akyurekli, Y., G. C. Taichman, D. L. White, W. J. Keon, Myocardial Responses to Sutureless Epicardial Lead Pacing, Proc. VIth World Symp. Cardiac Pacing, Montreal, , Meere, C., ed., PACESYMP, 1979, chap 33, No. 3.

Bourguignon, G. J. and L. Y. Bourguignon, Electric Stimulation of Proteins and DNA Synthesis in Human Fibroblasts, FASEB J., 1, 1987, p. 398-402.

Townsend, J.F., Stoeckle, H., and Schuder J.C., Tissue and Electrode Changes in Chronic Cardia Pacing—An Experimental Study, vol. XI Trans. Amer. Soc. Artif. Int. Organs, 1965, p. 132-138.

Cazeau, S , et al., "Four Chamber Pacing in Dilated Cardiomyopathy", *PACE, 17(Part II)*, (Nov. 1994), 1974-1979.

Daubert, Claude , "Permanent dual atrium pacing in major interatrial conduction blocks: a four years experience (Abstract 141)", *Pacing and clinical electrophysiology : PACE, 3(Part II)*, NASPE Abstracts—Abstract 141,(Apr. 1993),885.

Daubert, J C., et al., "Permanent left ventricular pacing with transvenous leads inserted into the coronary veins", *PACE, 21(Part II)*, (Jan. 1998),239-245.

Daubert, Claude , "Renewal of permanent left atrial pacing via the coronary sinus", *Pacing and clinical electrophysiology : PACE, 25(Part II)*, NASPE Abstracts—Abstract 255,(Apr. 1992),572.

Guidant, "Contak TR CHFD Model 1241", *System Guide*, Congestive Heart Failure Device,(1999),1-191.

Medtronic, "INSYNC III Device Model 8042", *Device Programming Guide*, INSYNC III Device Model 8042, Vision Programmer Software Model 9981,(2000),1-260.

Mitamura, H , et al., "Importance of the pacing mode in the initiation of ventricular tachyarrhythmia in a canine model of chronic myocardial infarction", *J Am Coll Cardiol., 6(1)*, (Jul. 1985),99-103.

St. Jude Medical, "Atlas + HF Models V-343, V-341", *User's Manual*, Implantable Cardioverter-Defibrillator,(Sep. 2003), 1-30.

St. Jude Medical, "Epic HF Model V-339", *User's Manual*, Implantable Cardioverter-Defibrillator,(Jul. 2002),1-26.

St. Jude Medical, "Model 3510 Programmer with Model 3307 Software", *Reference Manual*, For Atlas, Atlas+, Epic, Epic+, Photon u and Photon Implantable Cardioverter/Defibrillators,(Sep. 2003),1-314.

Steinhaus, David M., et al., "Anodal Stimulation: A Potential Concern with Biventricular Pacing?", *PACE, vol. 24, 553*, (Apr. 2001),3 pgs.

Stevenson, W G., et al., "Contribution of the anode to ventricular excitation during bipolar programmed electrical stimulation", *J. Am J Cardiol., 57(8)*, (Mar. 1, 1986),582-6.

Thakral, A , et al., "Effects of anodal vs. cathodal pacing on the mechanical performance of the isolated rabbit heart", *J. Appl Physiol., 89(3)*, (Sep. 2000),1159-64.

* cited by examiner

SYSTEM AND METHOD FOR PROVIDING TEMPORARY STIMULATION THERAPY TO OPTIMIZE CHRONIC ELECTRICAL PERFORMANCE FOR ELECTRODES USED IN CONJUNCTION WITH A CARDIAC RHYTHM MANAGEMENT SYSTEM

TECHNICAL FIELD

This invention relates to an implantable cardiac rhythm management system. In addition, the invention relates to a system and method for providing temporary stimulation therapy to optimize chronic electrical performance of implantable cardiac rhythm management systems.

BACKGROUND

Living tissues possess known bioelectrical properties. Potential differences can be observed in living tissues during normal function. For example, a potential difference (the "resting potential") of approximately −70 milliVolts exists between the inside and the outside of normal cell membranes. In certain specialized cell types, such as those found in the cardiac tissues, the potential difference across the cellular membrane slowly changes with time, eventually reaching a threshold that triggers rapid membrane depolarization.

The electrical characteristics of tissue are also observed in damaged tissues. The implantation of one or more pacing leads with electrodes for a cardiac rhythm management (CRM) system, such as a pacemaker or resynchronization device, involves trauma to the tissues, causing damage. This trauma may be caused at least in part by the simple placement of a pacing lead in heart tissue during normal CRM system implantation. More specifically, during implantation of a pacing lead for a CRM system, an elevation of the ST-segment of an electrocardiogram (ECG) is commonly observed, known as a repolarization abnormality, once contact between the electrode disposed at the end of the lead and the cardiac tissue is made. Also known as "current of injury," this repolarization abnormality may persist anywhere from only a few minutes to occasionally hours. The repolarization abnormality is therefore typically absent from prolonged ("chronic") lead performance.

It is known that an electrical stimulation applied to tissues may bring about desired effects. One obvious example is the use of electrical stimulation to bring about the clearly observable contraction of the heart muscle. Another much more subtle example is the use of electrical stimulation to alter the wound healing process.

It is also known in the art that electrical stimulation increases the healing rate in both animals and humans. Furthermore, evidence suggests that electrical stimulation can increase scar tissue development, encapsulation, and/or collagen deposition. Scar tissue development, encapsulation, and collagen deposition, generically referred to herein as a foreign body tissue response, are natural responses by a tissue to an implanted foreign object. For example, as shown in FIG. 1, a generic foreign object 100 implanted into a body tissue develops a fibrous encapsulation 110 around the foreign object's surface.

The research still further suggests that this foreign body tissue response, or healing enhancement, take place preferentially at the cathode. This may be significant because the cathode is the preferred polarity used for chronic cardiac stimulation in CRM devices such as pacemakers and resynchronization devices. It is believed that such a foreign body tissue response around a cathodic electrode alters voltage stimulation thresholds, or the voltage potential necessary to incite cardiac contraction. Specifically, as the natural tissue encapsulation surrounding an implanted electrode grows more extensive over time, the voltage needed to stimulate the tissue also increases. These studies show increased encapsulation with pacing and suggest undesirable alterations in electrical performance as a result of pacing.

The increased voltage stimulation thresholds associated with a foreign body tissue response are deleterious to a CRM system for several reasons. First, the higher voltages necessary for stimulation require greater current from the system's battery, thereby decreasing battery life for the system. Higher voltage stimulation may also impair the ability of the CRM system to rapidly sense the effectiveness of an electrical pulse communicated to stimulate the tissue. Further, higher voltage stimulation may result in electrochemical reactions at the electrode/tissue interface, the by-products of which possibly being toxic to the tissue.

FIG. 2 illustrates how typical voltage stimulation thresholds for two cathodic electrodes implanted in a heart tissue change over time. The voltage stimulation threshold is the voltage necessary to cause a desired effect on a tissue. For example, with cardiac tissue, the voltage stimulation threshold may be the voltage necessary to cause the cardiac tissue to contract. The x-axis in FIG. 2 represents time, in weeks, and the y-axis represents the voltage stimulation threshold necessary for stimulation of a cardiac tissue.

The first solid line A illustrates the voltage stimulation thresholds necessary for a typical electrode implanted into a cardiac tissue. A typical voltage stimulation threshold necessary to stimulate the tissue upon implantation is approximately 0.3 volts. As shown by line A, the stimulation threshold rises over the first two weeks of electrode implantation, peaking at approximately 1 to 2 volts, or possibly more. The stimulation threshold then plateaus and reaches a chronic threshold of approximately 1 volt after approximately four weeks of implantation.

The second dashed line B of FIG. 2 represents the voltage stimulation thresholds necessary for an implanted electrode that includes drug-eluting properties to counteract the foreign body tissue response after introduction of the electrode. One example of such a drug-eluting electrode is disclosed in U.S. Pat. No. 4,819,661 to Heil, Jr. et al., herein incorporated by reference in its entirety. One such drug that may be used to counteract the foreign body tissue response is a steroid. The voltage stimulation threshold for the drug-eluting electrode starts initially at the same 0.3 volts upon implantation, and the threshold peaks at approximately two weeks at approximately 0.8 volts. Finally, the stimulation threshold may reach a chronic level of approximately 0.7–0.8 volts at about four weeks. Therefore, although the drug-eluting electrode exhibits lower peak and chronic stimulation thresholds than a non drug-eluting electrode, there still exists a need to provide an electrode that exhibits still lower peak and chronic thresholds, as well as a lower threshold level at implantation.

It is believed that the mere act of pacing a heart from an implanted CRM system influences the type and rate of healing that occurs around the implanted electrode, causing a greater foreign body tissue response and encapsulation than if pacing was not performed. More specifically, the influence of cathodic pacing on promoting tissue encapsulation is believed to prevent optimized electrode performance. Optimized electrode performance may be achieved only when the tissue-promoting effects of pacing stimuli are minimized or eliminated.

It is therefore desirable to develop a system and method to decrease the foreign body tissue response to implanted electrodes and thereby decrease the voltage thresholds necessary to incite contraction.

SUMMARY

Generally, the present invention relates to an implantable cardiac rhythm management system. In addition, the invention relates to a system and method for providing temporary stimulation therapy to optimize chronic electrical performance of implantable cardiac rhythm management systems.

A cardiac rhythm management system for stimulating a human heart according to one aspect of the invention may include a sensing module coupled through at least one lead to an electrode associated with a tissue of the human heart for sensing electrical activity of the heart, a controller module coupled to the sensing module, wherein the controller module selects between a temporary stimulation therapy and a chronic stimulation therapy, and a therapy module coupled to the controller, wherein the therapy module communicates a plurality of anodic pulses to the heart through the lead when providing the temporary stimulation therapy.

According to another aspect of the invention, a cardiac rhythm management system for stimulating a human heart may include a sensing module coupled through at least one lead to an electrode associated with a tissue of the human heart for sensing electrical activity of the heart, a controller module coupled to the sensing module, wherein the controller module selects a selected therapy from at least two stimulation therapies including a temporary stimulation therapy and a chronic stimulation therapy, wherein the controller selects the temporary stimulation therapy upon implantation of the electrode and, after detection of an event, the controller module selects the chronic stimulation therapy, and a therapy module coupled to the controller, wherein the controller module communicates the selected stimulation therapy to the therapy module and wherein the therapy module communicates a plurality of electrical pulses to the heart, through the at least one lead, based on the selected stimulation therapy, wherein the therapy module provides anodic stimulation for the temporary stimulation therapy and cathodic stimulation for the chronic stimulation therapy.

According to yet another aspect of the invention, a method for reducing a tissue response to an implanted electrode used for stimulating a human heart may include steps of: stimulating the heart using a temporary stimulation therapy including anodic stimulation; detecting an event; and stimulating the heart using a chronic stimulation therapy including cathodic stimulation upon detection of the event.

In accordance with yet another aspect of the invention, a system for stimulating a human heart may include a means for communicating a plurality of anodic pulses to the heart; a means for determining when to transition from the plurality of anodic pulses to a plurality of cathodic pulses; and a means for communicating the plurality of cathodic pulses to the heart.

The above summary of the present invention is not intended to describe each disclosed embodiment or every implementation of the present invention. The figures and the detailed description that follow more particularly exemplify these embodiments.

DESCRIPTION OF THE DRAWINGS

The invention may be more completely understood in consideration of the following detailed description of various embodiments of the invention in connection with the accompanying drawings.

Figure 1:
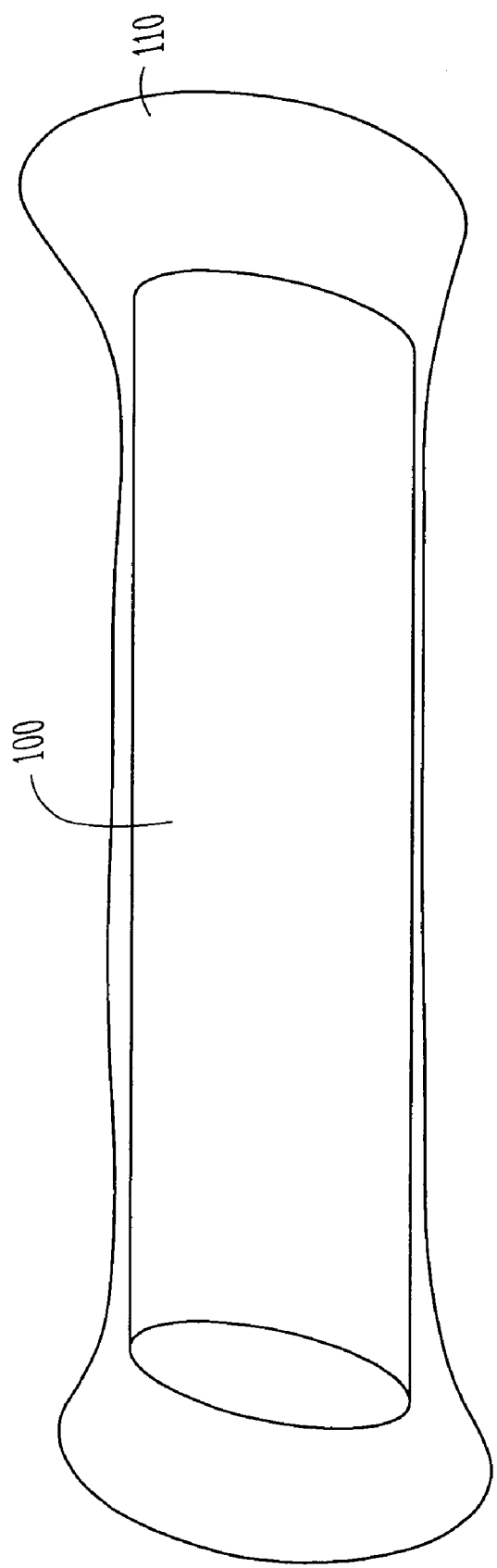
FIG. 1 is an illustration of an implanted body as encapsulated during a foreign body tissue response.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present invention relates to an implantable cardiac rhythm management (CRM) system. In particular, the present invention is directed to a system and method for providing temporary stimulation therapy to optimize chronic electrical performance for implantable CRM systems. While the present invention is not so limited, an appreciation of various aspects of the invention will be gained through a discussion of the examples provided below.

Figure 3:
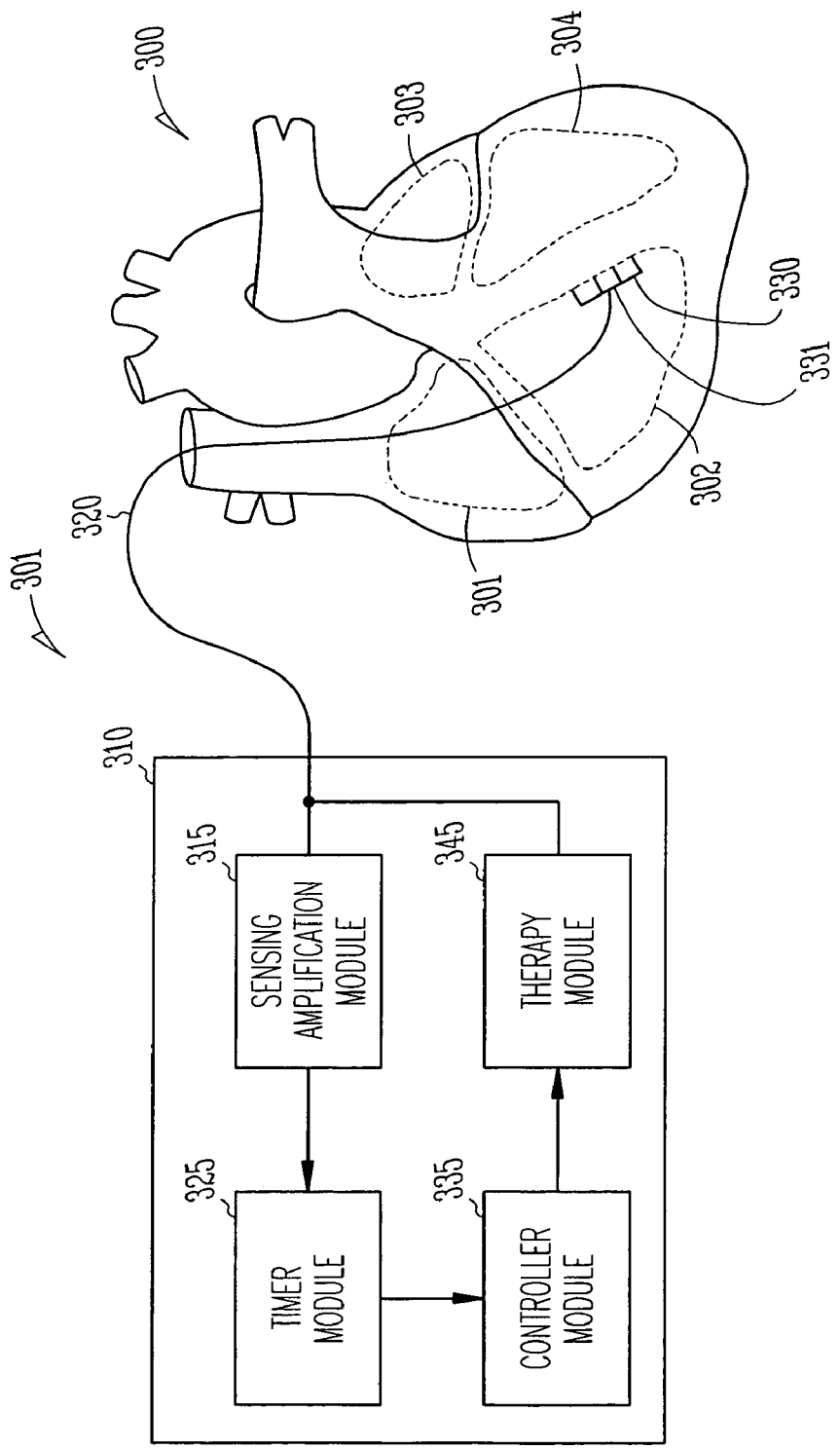
FIG. 3 is an schematic/block diagram of an implantable cardiac rhythm management system coupled to a heart in accordance with an example embodiment of the invention.

FIG. 3 is a schematic/block diagram illustrating one example embodiment of an implanted CRM system 301 made in accordance with the invention, as well as an environment in which the CRM system 310 is used. In this example embodiment, the CRM system 301 may include, among other components, a CRM device 310 that is coupled through one (or more) leads 320 to a heart 300 including a right atrium 301 and ventricle 302 and a left atrium 303 and ventricle 304. The CRM system 301 may be configured to provide a variety of therapies, such as, for example, pacing therapy, cardiac resynchronization therapy, and defibrillation, and may further be configured to implement one or more of the example methods performed in accordance with the present invention, as described below.

The lead 320 of the CRM system 300 includes an electrode 330. The electrode 330 may take a variety of forms, such as, for example, a tip electrode, a ring electrode, a housing electrode, or a header electrode. Other electrodes that are known by those skilled in the art may also be used. The electrode 330 may provide unipolar and/or bipolar (in conjunction with another electrode) sensing and/or therapy. The electrode 330, as illustrated, includes a drug-eluting submodule 331 as is known in the art. The drug-eluting submodule, as described above, may be used to deliver one or more drug substances to the tissue surrounding the electrode 330.

The electrode 330 is associated with the right ventricle 302 of the heart 300. The electrode 330 is "associated" with the particular heart chamber by inserting it into that heart chamber, or by inserting it into a portion of the heart's vasculature that is close to that heart chamber, or by epicardially placing the electrode outside that heart chamber, or by any other technique of configuring and situating an electrode for sensing signals and/or providing therapy with respect to that heart chamber. Epicardial sites of electrode placement can include not only the well-known sites within the right atrium 301 and the right ventricle 302 but also intravascular sites that drain the left side of the heart, such as the coronary sinus and great cardiac vein. Further, although the electrode 330 is shown positioned in the right ventricle 302, right atrial 301 and left atrial 303 and ventricular 304 placement may also be possible.

The CRM device 310 may include a plurality of modules typically included in a CRM device. In this example embodiment, the CRM device 310 includes a sensing/amplifier module 315, a timer module 325, a controller module 335, and a therapy module 345. The sensing/amplifier module 315, which is coupled to the heart 300 through the lead 320, senses the electrical activity of the heart as well as amplifies these sensed signals.

The timer module 325, which is coupled to the sensing/amplifier module 315, performs the timing requirements of the CRM device 310. The timer module 325 may be used to measure time intervals between heart contractions or other heart activity, as well as to measure time intervals between electrical pulses communicated to the heart by the CRM device 310.

The controller module 335, which is coupled to the timer module 325, may generally function to detect when a shift from anodic stimulation (the temporary stimulation therapy) to cathodic stimulation (the chronic stimulation therapy) should occur, and the controller module 335 may further cause a transition from anodic pulse generation to cathodic pulse generation. The controller module 335 may automatically detect when to transition from anodic stimulation to cathodic stimulation using one or more of the methods described below, or manual intervention may be necessary to cause the controller module 335 to initiate the transition.

The therapy module 345, which is coupled to the controller module 335, controls an output of the CRM device 310. The therapy module 345 may communicate one or more electrical pulses to the heart through the lead 320 or through one or more separate leads (not shown). The one or more electrical pulses may be anodic in polarity, may be cathodic in polarity, or may be a variety of anodic and cathodic pulses. The therapy module 345, in this example embodiment, is configured to implement one or more of the example methods described below in accordance with the present invention.

Figure 4:
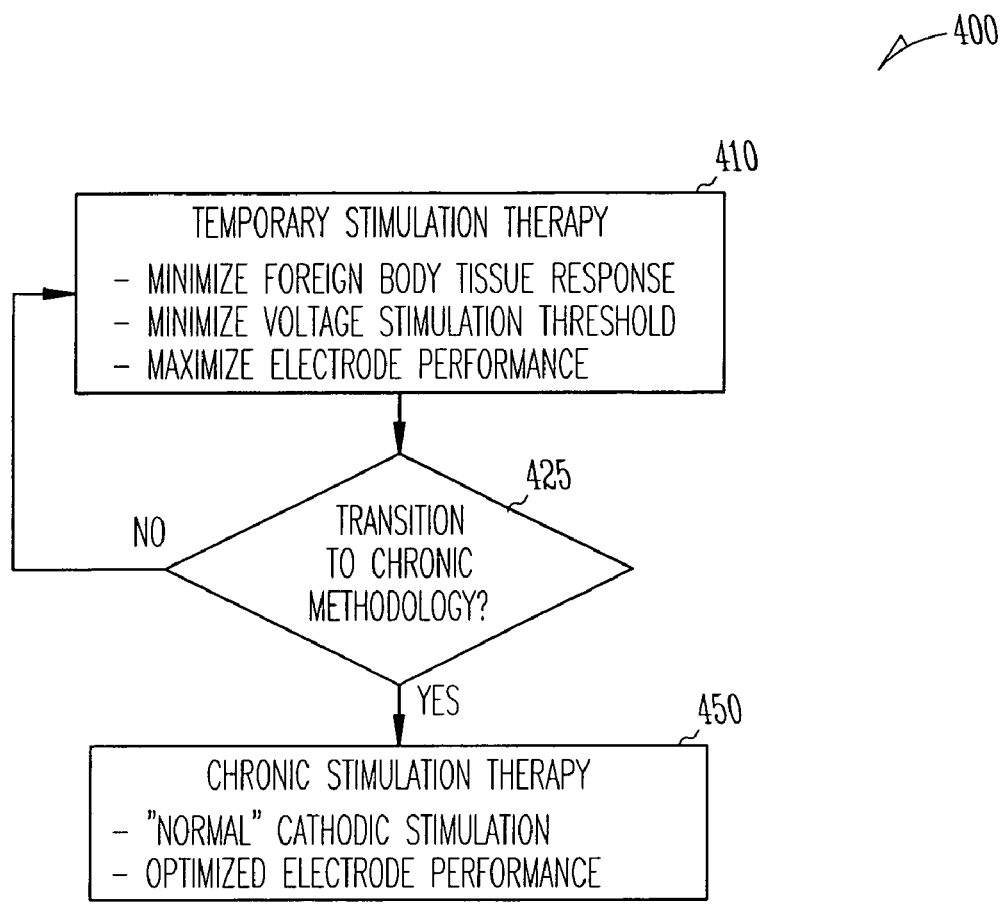
FIG. 4 is an example method for minimizing a foreign body tissue response in accordance with an embodiment of the invention.

The CRM system 301 may implement one or more methods to optimize electrode performance. Optimization of electrode performance may be achieved through use of an example method 400, as shown in FIG. 4, in accordance with an embodiment of the invention. The example method 400 may include a temporary stimulation therapy during which a foreign body tissue response is minimized for a selected therapy duration. As used herein, "therapy duration" means an interval of time during which a specific therapy is provided such as, for example, a four-week period. The example method 400 may also include a chronic stimulation therapy during which normal, or cathodic, stimulation may be performed for an indefinite therapy duration.

The method 400 may be used in conjunction with all stimulation electrodes intended for implantation. Specifically, the benefits from the method 400 may be applied to any electrodes positioned in or about the atria or ventricles of the heart at single or multiple stimulation sites. The abnormalities with which the method 400 may be utilized may include, without limitation, bradyarrhythmia, tachyarrhythmia, and congestive heart failure. Although specific electrode positions and abnormalities have been enumerated, the method 400, practiced in accordance with an example embodiment of the invention, may be applicable to any situation in which electrodes are implanted within a tissue.

The method 400 comprises an initial operation 410 including a temporary stimulation therapy and an operation 450 including a chronic stimulation therapy, as well as a decisional operation 425 functional to determine when the transition from the temporary stimulation therapy in operation 410 to the chronic stimulation therapy in operation 450 may occur. In operation 410, a temporary stimulation therapy is implemented during which the foreign body tissue response is minimized, thereby minimizing the voltage stimulation threshold necessary to incite cardiac contraction and maximizing electrode performance. Possible example embodiments of this temporary stimulation therapy as provided in operation 410 are discussed in detail below with reference to FIGS. 5–9.

During application of the temporary stimulation therapy in operation 410, control may be periodically passed to the decisional operation 425 in which a determination may be made as to when to transition from the temporary therapy of operation 410 to the chronic therapy of the operation 450. The methods employed by the operation 425 to make this determination are described in detail below. If operation 425 determines that a transition should be made from the temporary therapy of operation 410 to the chronic therapy of operation 450, control is passed to operation 450. Otherwise, control is returned to the operation 410. The operation 425 may be configured to periodically query as to whether to make the transition or not, or the operation 425 may make the transition after a specified event occurs, such as, for example, a specific therapy duration elapses.

After control is passed by operation 425 to operation 450, a chronic stimulation therapy is provided. The chronic stimulation therapy may include a known technique for tissue stimulation, such as cathodic stimulation of the tissue.

Figure 5:
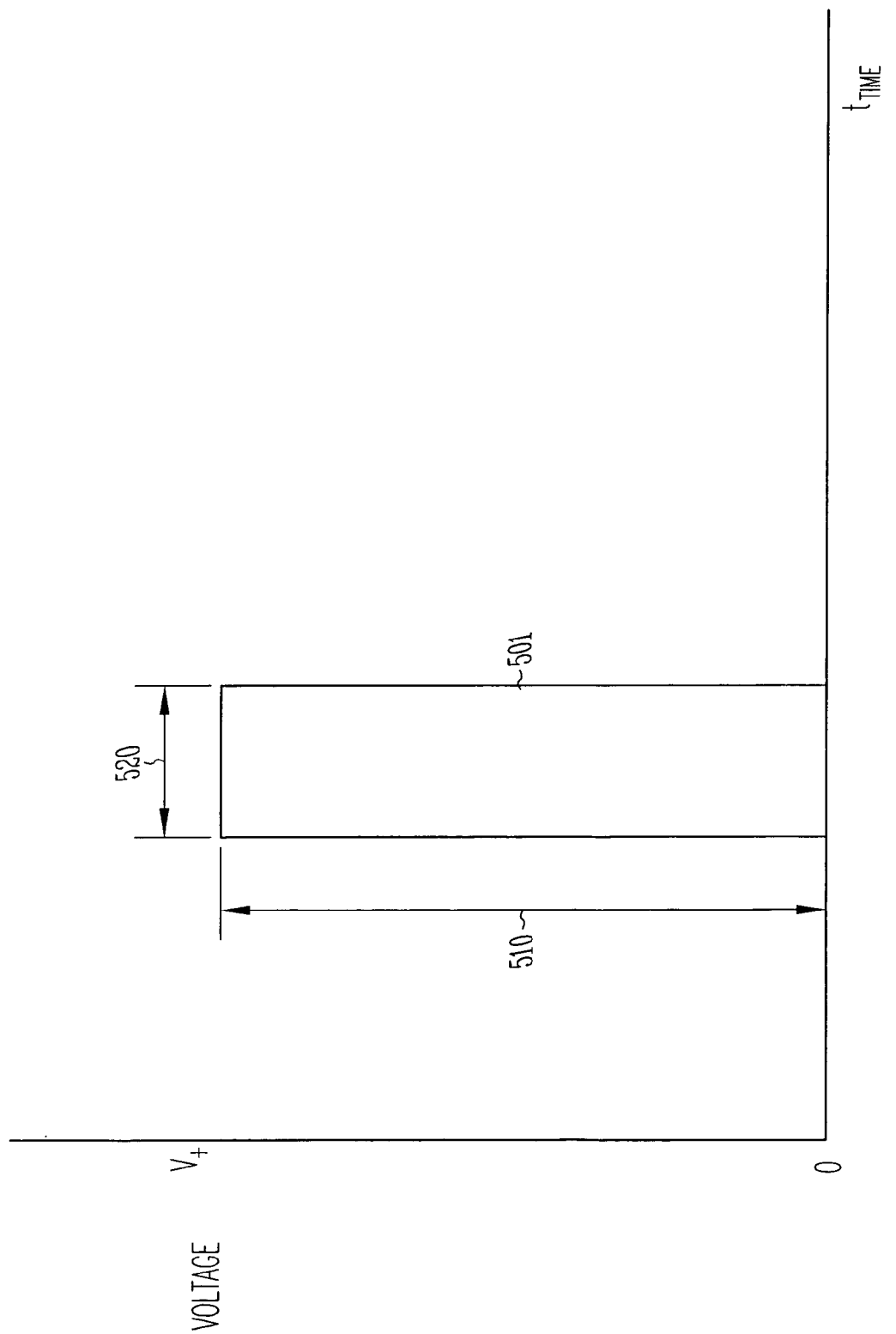
FIG. 5 is a graph illustrating an anodic pulse according to an example embodiment of the invention.

The temporary stimulation therapy of operation 410 may be implemented using a variety of techniques in accordance with example embodiments of the invention. One such example embodiment is illustrated in FIG. 5 and may include an anodic pulse 501 with an amplitude 510 and a pulse duration 520. The anodic pulse 501 is plotted on a graph with an x-axis representing time and a y-axis representing voltage and with the anodic polarity represented as a positive voltage and the cathodic polarity represented as a negative voltage.

An anodic pulse is generated by creating a potential at the electrode of a positive polarity. The amplitude 510 of the anodic pulse 501 represents the magnitude of the potential created. When the potential is of a sufficient magnitude, an electrical pulse is created. The amplitude 510 may be varied to exceed the voltage stimulation threshold of a given tissue and thereby create a desired effect, such as contraction of the heart muscle. The pulse duration 520 of the anodic pulse 501 is the duration of time during which the anodic pulse 501 is applied to the tissue. The pulse duration 520 may also be varied to create a desired effect, as described below. The range for the pulse duration 520 may be, for example, from 1 microsecond to 10 milliseconds. However, other durations are also possible. Typically, the pulse 501 would be applied at periodic intervals, such as, for example, once per heart contraction.

A distinct advantage is gained through use of an anodic pulse such as 501 rather than a cathodic pulse for stimulation of a tissue. Anodic stimulation, or the use of anodic pulses, does not appear to promote the wound healing aspects of the foreign body tissue response to the implanted electrode. Therefore, because the foreign body tissue response is attenuated using anodic stimulation, rather than encouraged as during cathodic stimulation, the chronic voltage stimulation thresholds may be decreased as a result. While it is recognized that anodic stimulation may require more energy than cathodic pacing and may promote inflammation of the associated tissues, use of anodic stimulation during a temporary stimulation therapy (such as is provided in operation 410) may result in a chronic stimulation therapy (such as in operation 450) exhibiting a reduced voltage stimulation threshold. Through variation in amplitude, duration, phase, and frequency of the anodic pulse 501, this reduction in chronic voltage stimulation threshold may be achieved.

A first scheme of anodic stimulation according to an example embodiment of the invention may involve providing an anodic pulse having a very rapid or short pulse duration 520 to bring about a desired tissue response, such as contraction. The anodic pulse duration 520 may be tailored to be very short in duration and thereby be practically invisible to any foreign body tissue response. In one example embodiment, the pulse duration 520 is preferably set to be between approximately 1 microsecond and 1000 microseconds, but it should be understood that variation in the pulse duration 520 is possible.

A second scheme of anodic stimulation according to another example embodiment of the invention may include anodic stimulation using, for example, the anodic pulse 501 as illustrated in FIG. 5, along with a drug delivered by a drug-eluting electrode. The drug-eluting capabilities of the electrode may be used to combat the recruitment of inflammatory cells that anodic stimulation may cause. The drug-eluting electrode may deliver local anti-inflammatory drug therapy to the tissue. This drug therapy may include drugs known to suppress inflammatory cell function, such as anti-inflammatory steroids including, but not limited to, dexamethasone, betamethasone, hydrocortison, and/or beclomethasone, as well as drugs known to eliminate inflammatory cells or cell function, such as a bisphosphonate exhibiting cytotoxic properties specific to the inflammatory cells, for example. A combination of two or more suppressive and/or cytotoxic drugs may also be used.

In addition to varying the type of drug used to combat inflammation, the drug delivery method may also be varied. For example, the drug-eluting electrode may first provide a local drug substance to the tissue by means of simple passive diffusion. The anti-inflammatory drugs may subsequently be delivered into the cells through other means, such as iontophoresis or electroporation. In many cases, the physical and/or chemical properties of candidate pharmaceutical substances prohibit the delivery of drug substances into tissues. Iontophoresis uses the electric field developed by the electrode to inject the drug substance deep into tissues. Also, the physical and/or chemical properties of candidate drug substances may prohibit the entry of agents into the cells by simple passive diffusion. Electroporation involves using a stimulation pulse of such amplitude to form one or more large pores within a cell membrane and thereby facilitates diffusive entry of the drugs into the cells. The amplitude 510 and a pulse duration 520 of an anodic pulse 501 can be selected to also cause electroporation of the excited tissues and thereby facilitate drug delivery to the cells of the excited tissues. It may even be possible to utilize this effect to inject the cells with drug substances without bringing about heart contraction.

In yet another variation of the method, the drug release duration may be varied, following system implantation, during which the electrode releases the anti-inflammatory drugs. For example, the drug release duration by a drug-eluting electrode may be set to coincide with or be slightly longer than a pulse duration of the anodic pulse, which is believed to cause the typical healing response that brings about the undesired elevation of the stimulation threshold. In this manner, drug release may occur over a period of time that would counteract the possible inflammatory side effects of anodic stimulation.

Figure 6:
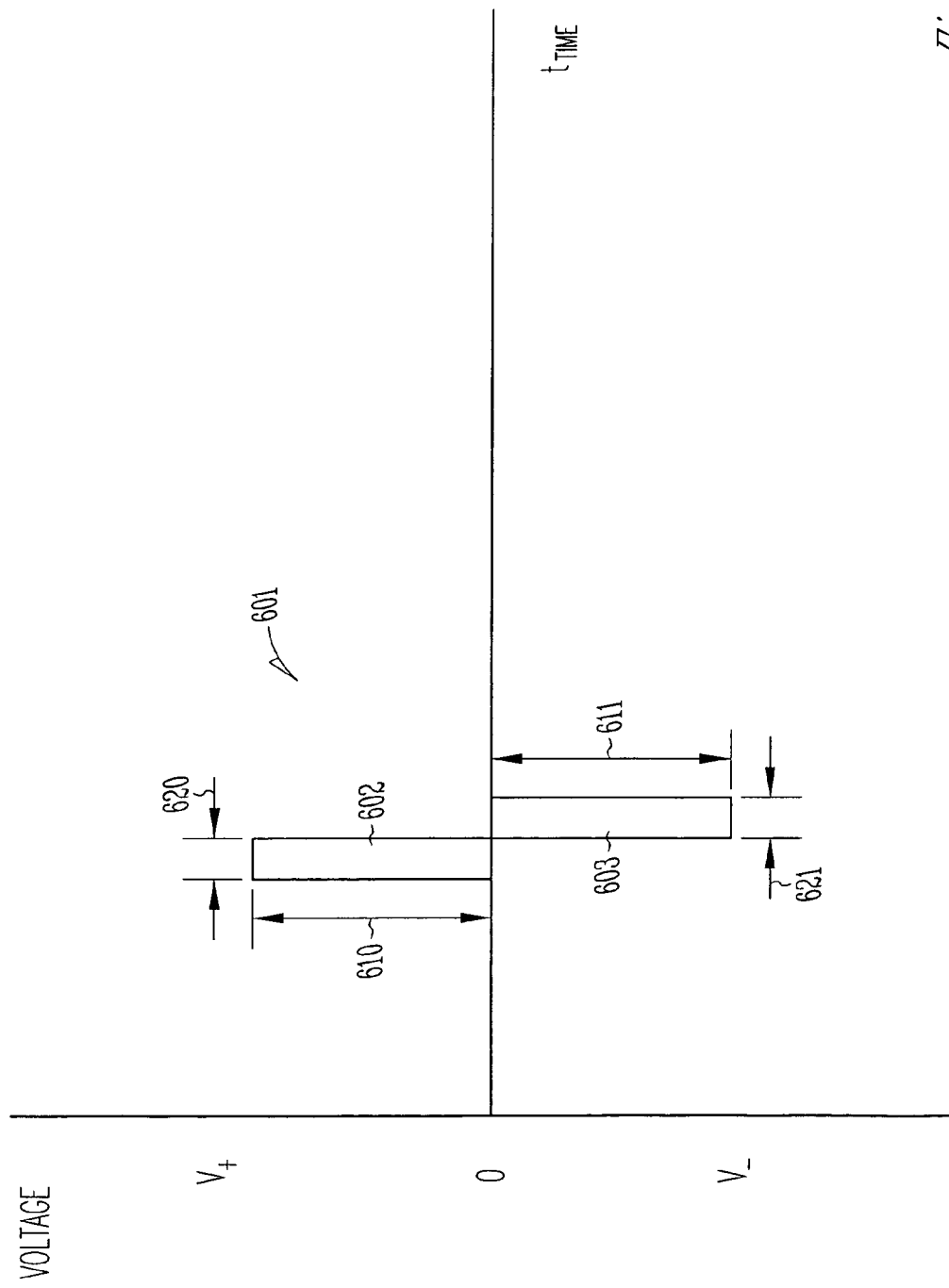
FIG. 6 is a graph illustrating a biphasic pulse according to an example embodiment of the invention.

A third scheme utilizing anodic stimulation according to another example embodiment of the invention may involve biphasic stimulation. Biphasic stimulation may include a pulse exhibiting both cathodic and anodic polarity components, as is illustrated in FIG. 6. In FIG. 6, a biphasic pulse 601 includes an anodic component 602 with an amplitude 610 and a pulse duration 620 and a cathodic component 603 with an amplitude 611 and a pulse duration 621. The biphasic pulse 601 may be varied in sequence (i.e. the anodic component 602 may be communicated before the cathodic component 603 or vice versa), placement (i.e. the anodic component 602 and the cathodic component 603 may be implemented consecutively, as shown, or a pause may be provided between the anodic component 602 and the cathodic component 603, see, e.g., FIGS. 7–9), amplitude (i.e. amplitudes 610 and 611 may be equal or unequal), and pulse duration (i.e. the pulse durations 620 and 621 may be equal or unequal) to define an optimal healing waveform. In one example embodiment, the biphasic pulse is generated to have equal cathodic and anodic components, as shown. However, variations in the cathodic and anodic components may be practiced without departing from the scope of the invention. Further, a drug-eluting electrode may also be utilized with any scheme of stimulation to provide drug therapy, as described above.

Figure 7:
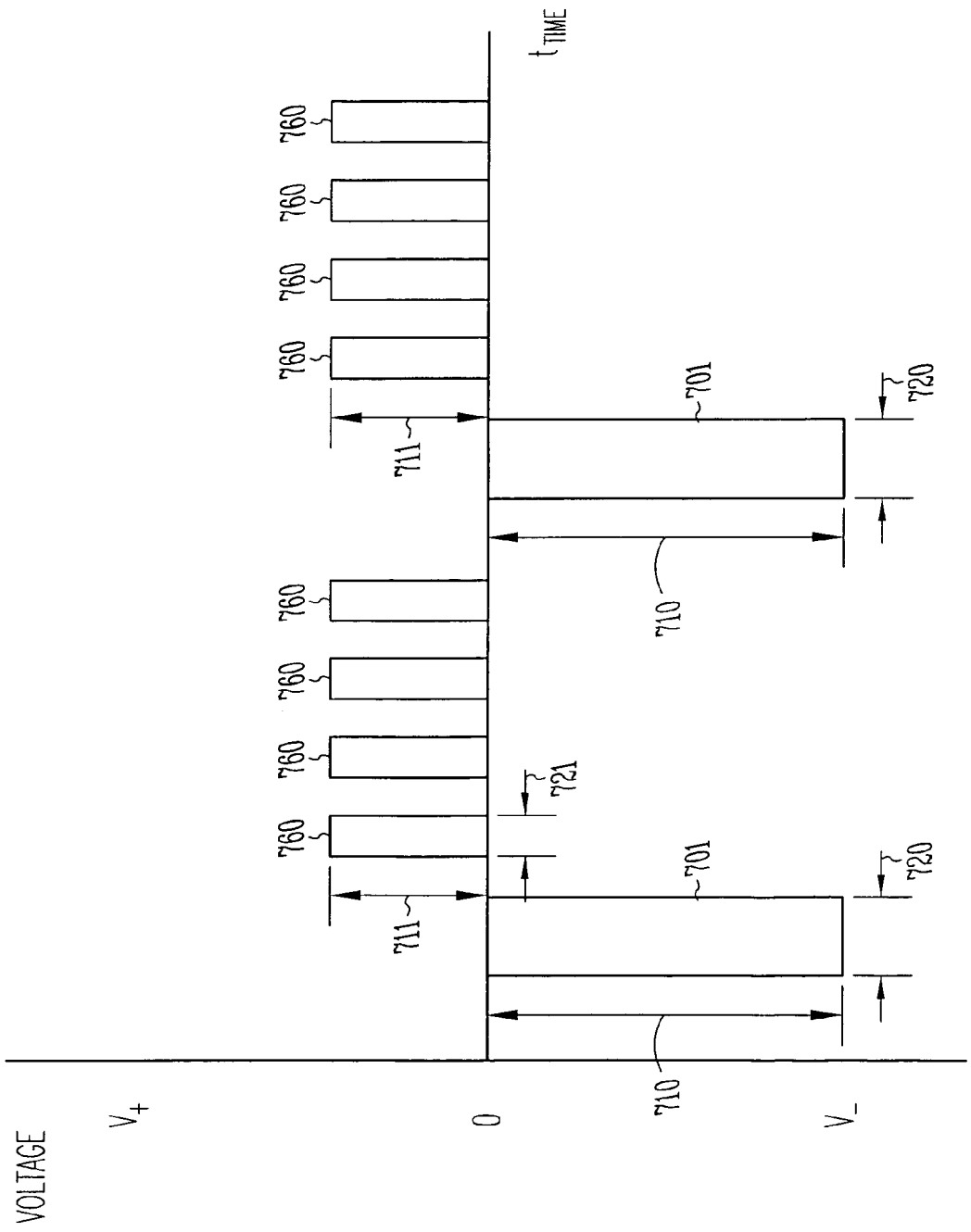
FIG. 7 is a graph illustrating a series of cathodic pulses with an associated trailing train of subthreshold anodic pulses according to an example embodiment of the invention.

In a variation on the biphasic stimulation scheme in accordance with another example embodiment of the invention, a biphasic waveform as shown in FIG. 7 may be used to minimize foreign body tissue response. FIG. 7 includes a series of cathodic pulses 701 with one or more subthreshold anodic pulses 760 interspersed between adjacent cathodic pulses 701. In this embodiment, the cathodic pulses 701 may be of sufficient amplitude 710 to exceed the voltage stimulation threshold and thereby stimulate the tissue. Interspersed between the cathodic pulses 701 can be a train of subthreshold anodic pulses 760 with amplitudes 711 to be below the voltage stimulation threshold of the tissue and therefore not significantly contribute to tissue stimulation.

The pulse amplitudes 710 and 711 and pulse durations 720 and 721 may be varied, as well as the frequency of the subthreshold pulses, to minimize encapsulation caused during the foreign body tissue response. For example, in FIG. 8, cathodic pulses 801 are followed by a train of subthreshold anodic pulses 860, 861, 862, and 863 with varying amplitudes. The amplitudes of subthreshold anodic pulses 860, 861, 862, and 863, as shown in FIG. 8, gradually decrease, with the greatest amplitude anodic pulses 860 being delivered very shortly after the cathodic pulses 801 that causes tissue stimulation.

Figure 9:
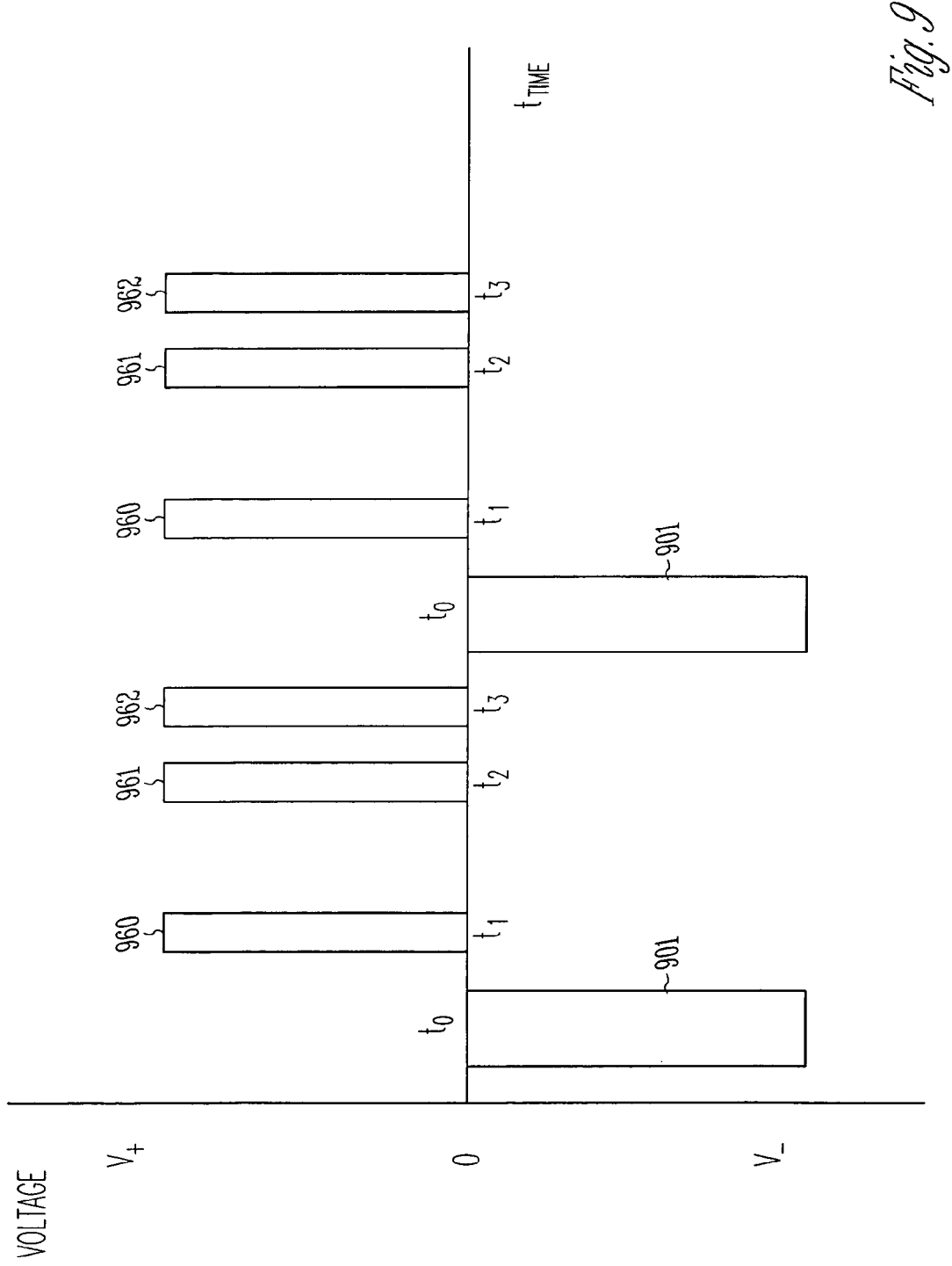
FIG. 9 is a graph illustrating yet another series of cathodic pulses with an associated trailing train of subthreshold anodic pulses of varying frequency according to an example embodiment of the invention.

In another example as shown in FIG. 9, cathodic pulses 901 causing tissue stimulation are followed by anodic subthreshold pulses 960, 961, and 962. The frequency of the anodic pulses is varied, with subthreshold anodic pulse 960 at time $t_1$, 961 at time $t_2$, and 962 at time $t_3$.

Figure 8:
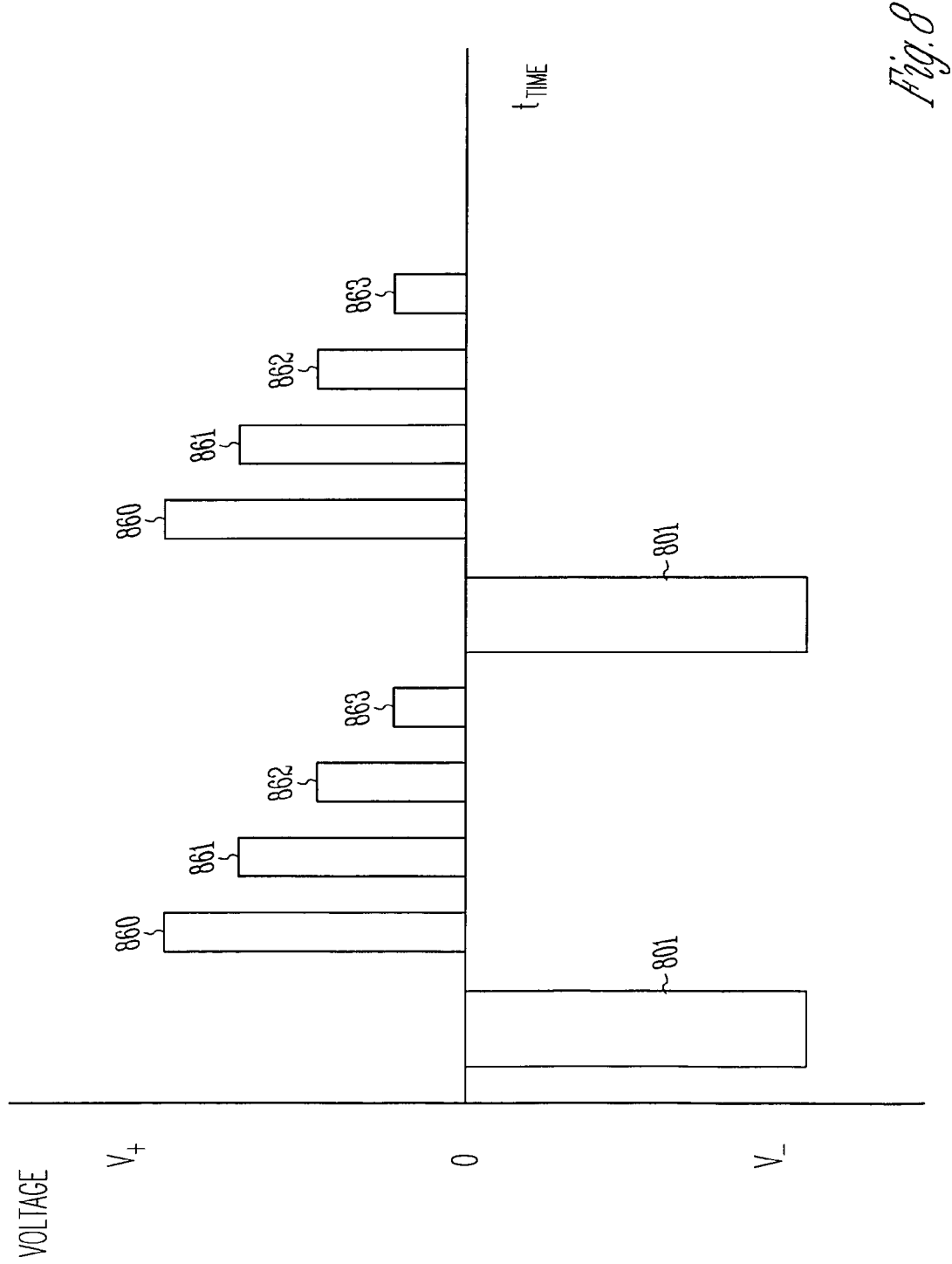
FIG. 8 is a graph showing another series of cathodic pulses with an associated trailing train of subthreshold anodic pulses of varying amplitude according to an example embodiment of the invention.

It should be understood that the embodiments provided in FIGS. 7–9 are by way of example only and that variation in the amplitude, duration, frequency, and phase of both the cathodic and anodic pulses may be achieved without departing from the spirit of the invention. In this manner, cathodic and anodic simulation may be tailored to minimize the foreign body tissue response and thereby maximize electrode performance.

Figure 2:
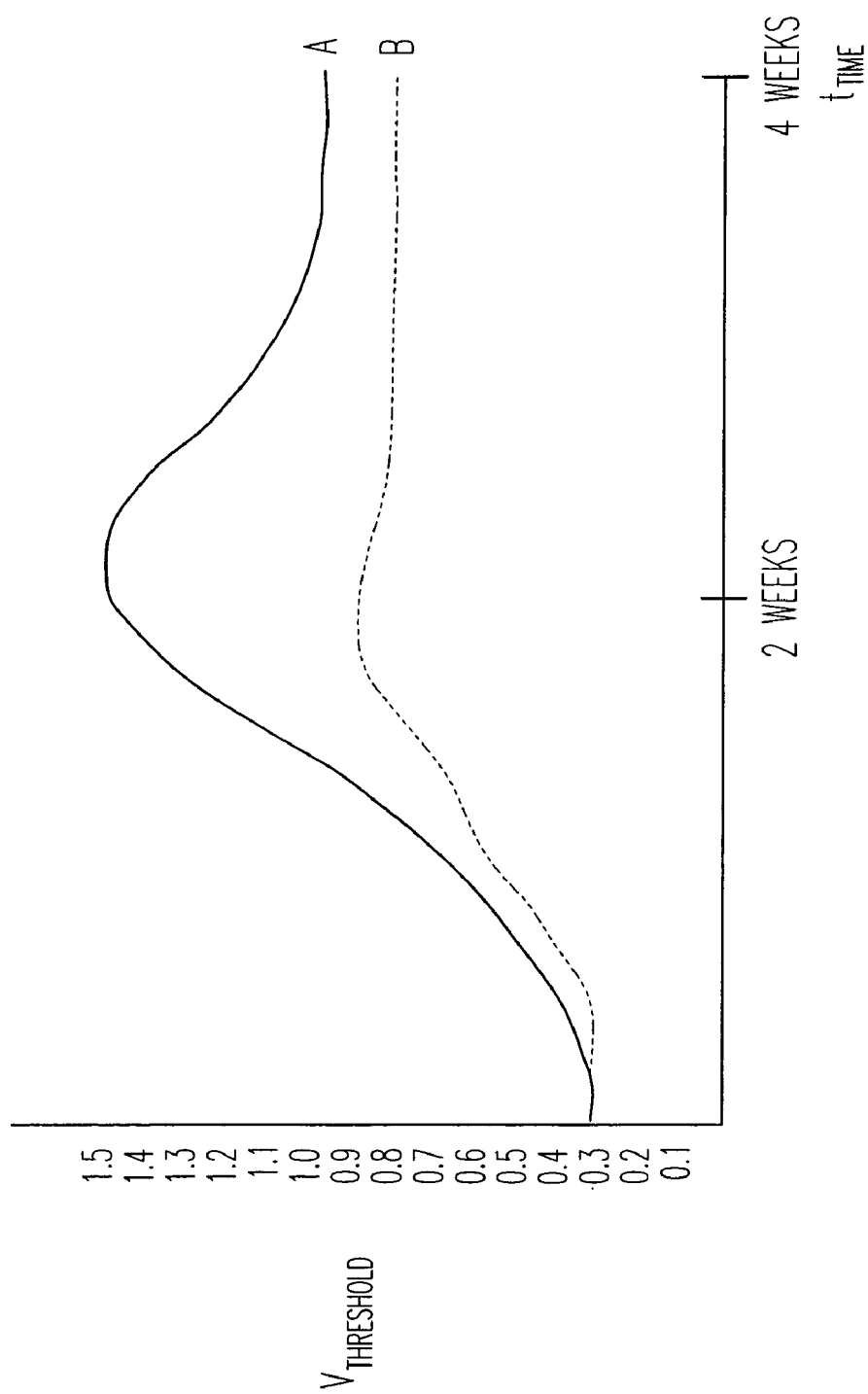
FIG. 2 is a graph showing voltage stimulation thresholds for a non-drug-eluting and a drug-eluting electrode.

Referring once again to FIG. 4, in which the example method 400 is provided in accordance with the present invention, the temporary stimulation therapy in operation 410 is followed by the chronic stimulation therapy in operation 450. The transition from operation 410 to operation 450 is controlled, such as by the controller module 335 in FIG. 3, in operation 425. The transition may be initiated after a specified therapy duration, such as when chronic stimulation threshold levels are reached at approximately the four-week point, as shown in FIG. 2, or by monitoring specific parameters, such as electrode impedance or voltage stimulation levels, as described below.

The transition from the temporary stimulation therapy to the chronic therapy may be executed after such physiological measurements as the impedance across a stimulating electrode, such as the electrode 330, reaches a given level. It is known that after electrode implantation, the inflammatory process may cause electrode impedance levels to quickly drop to a minimum in the first few days followed by a gradual return to impedance values observed at implantation. Therefore, in this example method, electrode impedance could be monitored, and transition from the temporary therapy in operation 410 to the chronic therapy in operation 450 may be accomplished when electrode impedance levels return to approximately implantation levels.

In yet another variation, the time period at which to transition between the temporary and chronic stimulation therapies may be determined through monitoring the voltage simulation thresholds themselves. As illustrated previously in FIG. 2, voltage stimulation thresholds initially increase, then peak, and finally decrease to a chronic level. Once voltage simulations thresholds have stabilized at the chronic level, transition from operation 410 to 450 may be achieve. Therefore, the controller module 335 may be implemented to monitor the voltage stimulation threshold levels and transition to the chronic therapy when the voltage stimulation thresholds reach a certain level. A combination of monitoring both impedance and voltage stimulation thresholds may also be used for measuring when to transition between therapies.

The transition from the temporary stimulation therapy of operation 410 to the chronic therapy of operation 450 marks the stabilization of the benefits provided by anodic stimulation. When the temporary stimulation therapy has been completed, the foreign body tissue response has been minimized, thereby minimizing encapsulation and maximizing electrode performance. At this stage, the switch to chronic stimulation in operation 450, utilizing traditional cathodic stimulation, can be performed.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the instant specification.

What is claimed is:

1. A cardiac rhythm management system for stimulating a human heart, the system comprising:
   a sensing module coupled through at least one lead to an electrode associated with a tissue of the human heart for sensing electrical activity of the heart;
   a controller module coupled to the sensing module, wherein the controller module selects between a temporary stimulation therapy and a chronic stimulation therapy; and
   a therapy module coupled to the controller, wherein the therapy module communicates a plurality of anodic pulses to the heart through the lead when providing the temporary stimulation therapy;
   wherein the system initially operates using the temporary stimulation therapy and wherein the controller, upon detection of an event, selects the chronic stimulation therapy.

2. The system of claim 1, wherein a pulse duration of each of the plurality of anodic pulses is less than 1000 microseconds.

3. The system of claim 1, wherein the electrode further comprises a drug-eluting submodule, wherein the drug-eluting submodule releases at least one drug.

4. The system of claim 3, wherein the at least one drug includes an anti-inflammatory drug.

5. The system of claim 3, wherein timing for the release of the at least one drug by the drug-eluting submodule is set to coincide with a pulse duration of each of the plurality of anodic pulses.

6. The system of claim 3, wherein an amplitude of each of the plurality of anodic pulses is of sufficient magnitude to facilitate delivery of the drug.

7. The system of claim 1, wherein the therapy module further generates a plurality of cathodic pulses interspersed within the plurality of anodic pulses.

8. The system of claim 7, wherein each of the plurality of cathodic pulses is followed by at least one subthreshold anodic pulse from the plurality of anodic pulses.

9. The system of claim 7, wherein each of the plurality of cathodic pulses is followed by a train of subthreshold anodic pulses.

10. The system of claim 9, wherein an amplitude of each anodic pulse of the train of subthreshold anodic pulses is varied.

11. The system of claim 1, wherein the chronic stimulation therapy includes a plurality of cathodic pulses.

12. The system of claim 1, wherein the event is the stabilization of an impedance across the electrode.

13. The system of claim 1, wherein the event is the stabilization of a voltage stimulation threshold necessary to stimulate the heart tissue.

14. The system of claim 1, wherein the therapy module varies an amplitude of each of the plurality of anodic pulses.

15. The system of claim 1, wherein the therapy module varies a frequency of each of the plurality of anodic pulses.

16. The system of claim 1, wherein the therapy module varies a pulse duration of each of the plurality of anodic pulses.

17. A cardiac rhythm management system for stimulating a human heart, the system comprising:
   a sensing module coupled through at least one lead to an electrode associated with a tissue of the human heart for sensing electrical activity of the heart;
   a controller module coupled to the sensing module, wherein the controller module selects a selected therapy from at least two stimulation therapies including a temporary stimulation therapy and a chronic stimulation therapy, wherein the controller selects the temporary stimulation therapy upon implantation of the electrode and, after detection of an event, the controller module selects the chronic stimulation therapy; and
   a therapy module coupled to the controller, wherein the controller module communicates the selected stimulation therapy to the therapy module and wherein the therapy module communicates a plurality of electrical pulses to the heart, through the at least one lead, based on the selected stimulation therapy, wherein the therapy module provides anodic stimulation for the temporary stimulation therapy and cathodic stimulation forte chronic stimulation therapy.

18. A method for reducing a tissue response to an implanted electrode used for stimulating a human heart, the method comprising steps of:
   stimulating the heart using a temporary stimulation therapy including anodic stimulation;
   detecting an event; and
   stimulating the heart using a chronic stimulation therapy including cathodic stimulation upon detection of the event.

19. The method of claim 18, wherein the temporary stimulating step further comprises a step of generating an anodic pulse such that a pulse duration of the anodic pulse is short.

20. The method of claim 19, wherein the generating step further comprises a step of creating the anodic pulse such that the pulse duration of the anodic pulse is less than 1000 microseconds.

21. The meted of claim 18, further comprising steps of:
   releasing a drug using a drug-eluting electrode; and
   applying an anodic pulse of an amplitude such that the anodic pulse will both stimulate the heart and create electroporation to facilitate diffusion of the drug into the tissue.

22. The method of claim 18, further comprising a step of timing a release of a drug to coincide with a pulse duration of an anodic pulse.

23. The method of claim 18, farther comprising steps of:
   releasing a drug exhibiting anti-inflammatory characteristics; and
   allowing the drug to diffuse across a membrane of at least one cell of the tissue.

24. The method of claim 23, wherein the releasing step further comprises a step of selecting a bisphosphonate as the drug.

25. The method of claim 18, further comprising steps of:
   releasing a combination of drugs exhibiting anti-inflammatory suppressive and cytotoxic characteristics; and
   allowing the combination of drugs to diffuse across a membrane of the tissue surrounding the electrode.

26. The method of claim 18, wherein the temporary stimulating step further comprises a step of providing temporary stimulation therapy including biphasic stimulation.

27. The method of claim 26, wherein the providing step further comprises a step of forming a biphasic pulse to include equal cathodic and anodic components.

28. The method of claim 26, wherein the providing step further comprises a step of forming the biphasic stimulation to include a plurality of cathodic pulses and at least one subthreshold anodic pulse interspersed between adjacent cathodic pulses.

29. The method of claim 28, wherein the forming step further comprises varying an amplitude of the at least one subthreshold anodic pulse.

30. The method of claim 28, wherein the forming step further comprises varying a frequency of the at least one subthreshold anodic pulse.

31. The method of claim 28, wherein the forming step further comprises generating a plurality of subthreshold anodic pulses between each adjacent cathodic pulse, wherein a subthreshold anodic pulse following a cathodic pulse is greater in amplitude than other of the plurality of anodic pulses between each adjacent cathodic pulse.

32. The method of claim 18, wherein the detecting step further comprises steps of:
   defining the event as a change in an impedance of the electrode; and
   measuring the impedance of the electrode to determine when the impedance reaches an initial implantation level.

33. The method of claim 18, wherein the detecting step further comprises steps of:
   defining the event as a change in voltage stimulation threshold; and
   monitoring voltage stimulation thresholds to determine when the voltage stimulation threshold stabilizes.

* * * * *

UNITED STATES PATENT AND TRADEMARK OFFICE
CERTIFICATE OF CORRECTION

PATENT NO. : 7,110,815 B2
APPLICATION NO. : 10/139916
DATED : September 19, 2006
INVENTOR(S) : Heil, Jr. et al.

It is certified that error appears in the above-identified patent and that said Letters Patent is hereby corrected as shown below:

In column 11, line 28, in Claim 17, delete "forte" and insert -- for the --, therefor.

In column 11, line 47, in Claim 21, delete "meted" and insert -- method --, therefor.

In column 12, line 1, in Claim 23, delete "farther" and insert -- further --, therefor.

Signed and Sealed this

Nineteenth Day of December, 2006

JON W. DUDAS
*Director of the United States Patent and Trademark Office*